US00PP34821P2

(12) United States Plant Patent
Maria de Jong

(10) Patent No.: US PP34,821 P2
(45) Date of Patent: Dec. 13, 2022

(54) CHERRY LAUREL PLANT NAMED 'JOPRU3'

(50) Latin Name: *Prunus laurocerasus*
Varietal Denomination: JOPRU3

(71) Applicant: Cornelis Henricus Maria de Jong, Biezenmortel (NL)

(72) Inventor: Cornelis Henricus Maria de Jong, Biezenmortel (NL)

( * ) Notice: Subject to any disclaimer, the term of this patent is extended or adjusted under 35 U.S.C. 154(b) by 0 days.

(21) Appl. No.: 17/857,603

(22) Filed: Jul. 5, 2022

(51) Int. Cl.
*A01H 5/12* (2018.01)
*A01H 6/74* (2018.01)

(52) U.S. Cl.
USPC ..... Plt./226
CPC ..... *A01H 6/7427* (2018.05)

(58) Field of Classification Search
USPC ..... Plt./226
CPC ..... A01H 6/7427; A01H 5/00; A01H 5/02; A01H 5/12
See application file for complete search history.

*Primary Examiner* — Keith O. Robinson
(74) *Attorney, Agent, or Firm* — Weatherly IP Solutions, LLC; Barbara Campbell

(57) ABSTRACT

A new cherry laurel plant particularly distinguished by having a flattened globular plant shape with a broad spreading-upright habit and green and yellow-green foliage, is disclosed.

3 Drawing Sheets

Genus and species: *Prunus laurocerasus.*
Variety denomination: 'JOPRU3'.

BACKGROUND OF THE NEW PLANT

The present invention comprises a new and distinct variety of cherry laurel plant, botanically known as *Prunus laurocerasus*, and hereinafter referred to by the variety name 'JOPRU3'. 'JOPRU3' originated from an open-pollination conducted in Biezenmortel, The Netherlands, July 2011 between un-named and unpatented *Prunus laurocerasus* parent plants.

The seeds from the open-pollination were sown and plants were grown outdoors for evaluation, where an individual plant designated 'JOPRU3' was selected from the group of plants in Biezenmortel, The Netherlands, in 2013. In November 2017, 'JOPRU3' was first vegetatively propagated by softwood cuttings. 'JOPRU3' was found to reproduce true to type in successive generations of asexual propagation via softwood cuttings.

SUMMARY

The following are the most outstanding and distinguishing characteristics of this new variety when grown under normal horticultural practices in Biezenmortel, The Netherlands.

1. A flattened globular plant shape with a broad spreading-upright habit; and
2. Green and yellow-green foliage.

DESCRIPTION OF THE PHOTOGRAPHS

This new cherry laurel plant is illustrated by the accompanying photographs which show the plant's overall plant habit including form, and foliage. The photographs are of a 4.5-year-old plant grown outdoors in Biezenmortel, The Netherlands and taken in May 2022. The colors shown are as true as can be reasonably obtained by conventional photographic procedures.

Figure 1:
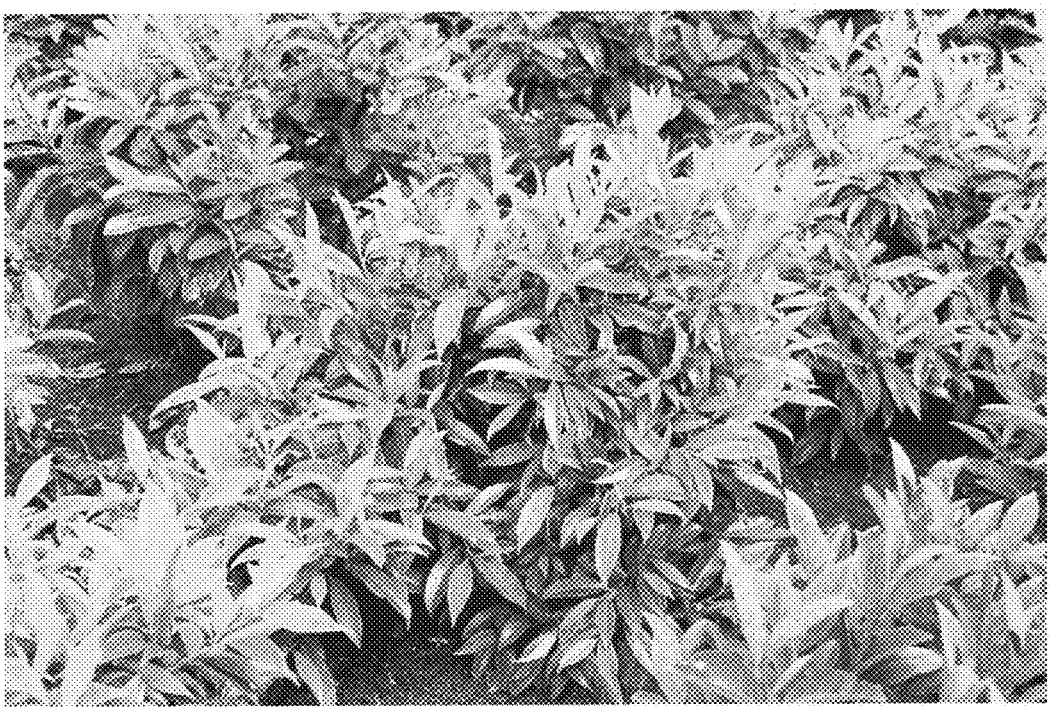
Figure 2:
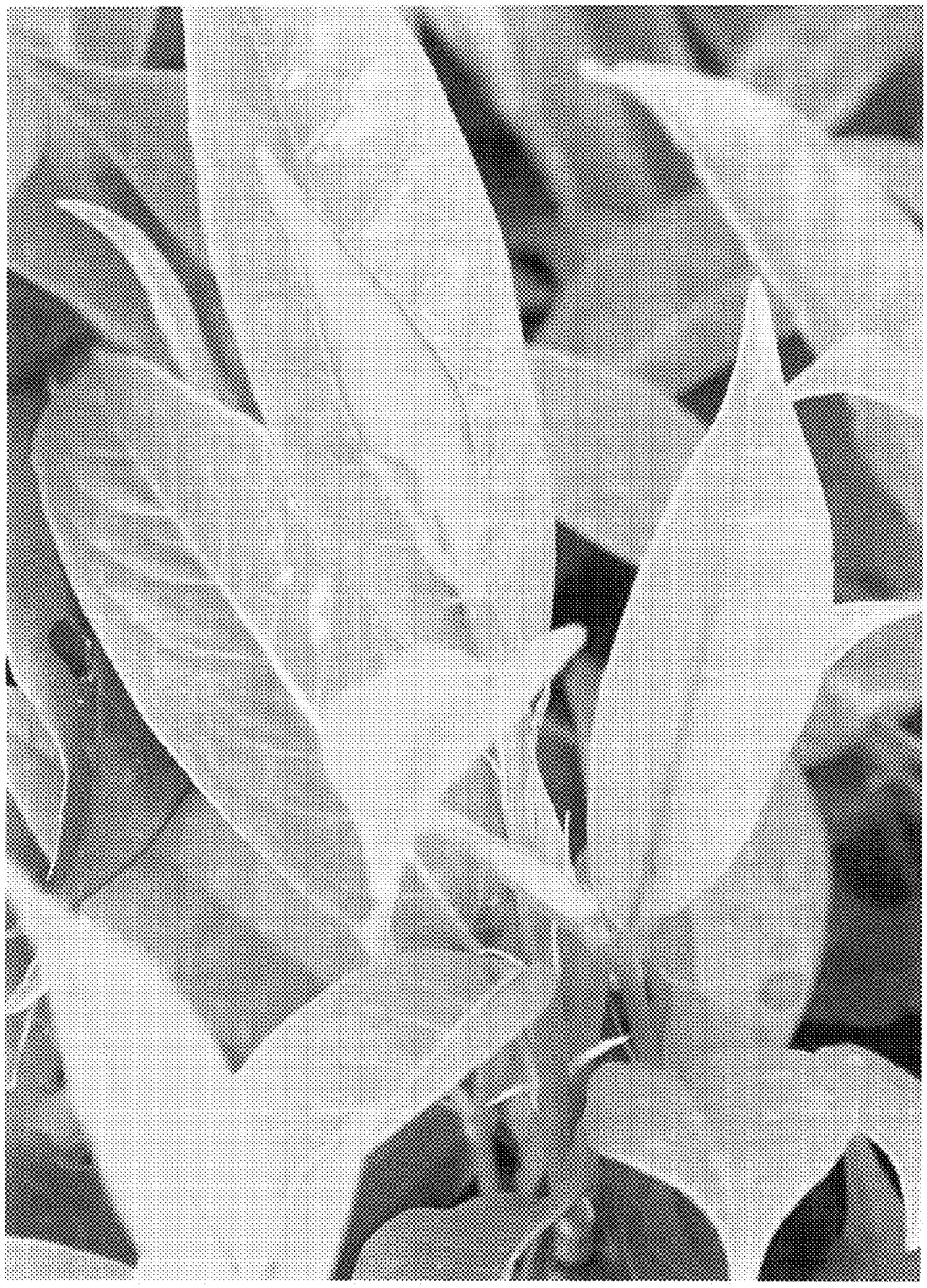
Figure 3:
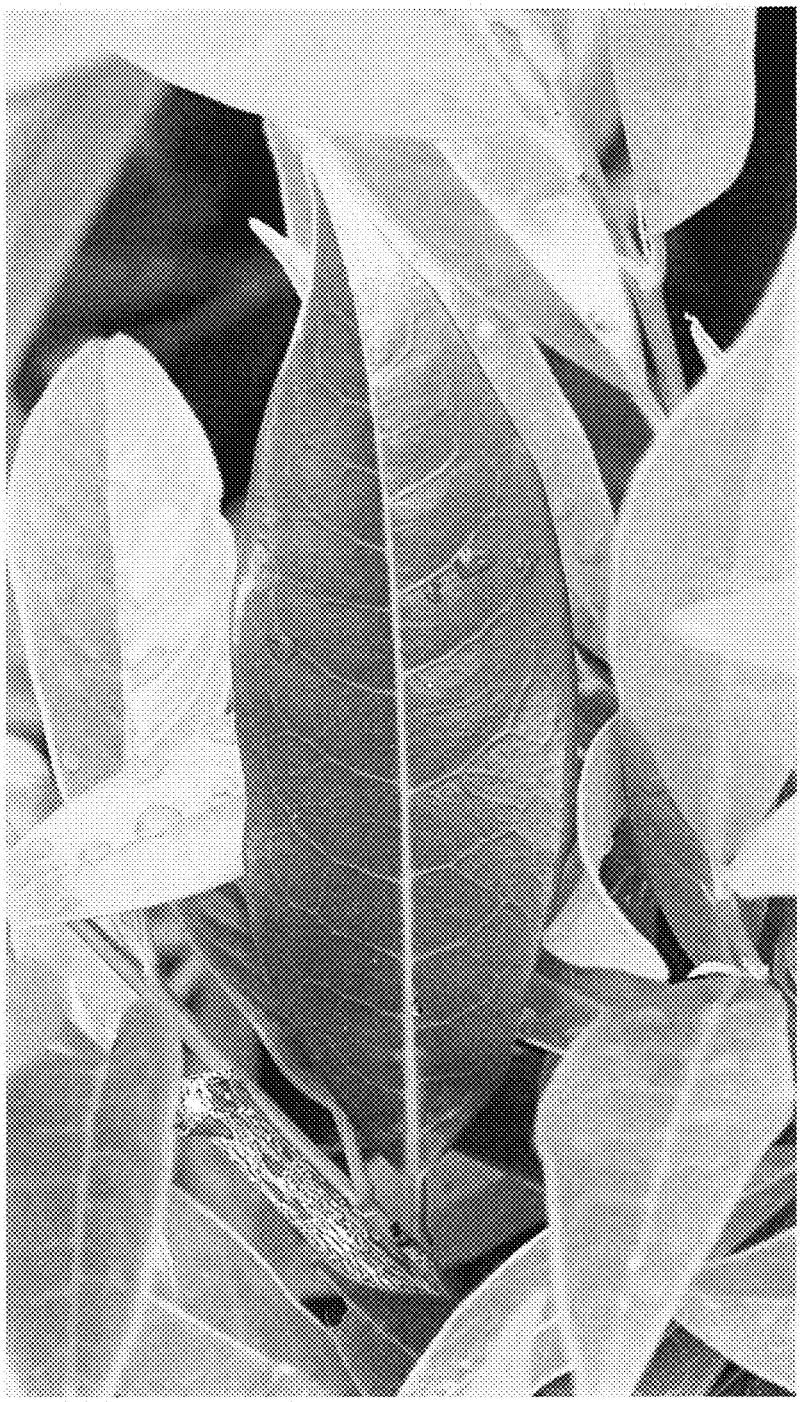

FIG. 1 shows the overall plant habit of 'JOPRU3'.
FIG. 2 shows a close-up of the new growth.
FIG. 3 shows a close-up of an individual mature leaf.

DESCRIPTION OF THE NEW VARIETY

The following detailed descriptions set forth the distinctive characteristics of 'JOPRU3'. The data which define these characteristics were collected from asexual reproductions carried out in The Netherlands. Data was collected on 4.5-year-old plants grown outdoors in Biezenmortel, The Netherlands in May 2022. The range of day temperatures was 14° C. to 24° C. and the range of night temperatures was 4° C. to 12° C. Plants were deeply pruned in late October 2020 and late October 2021. Color references are to The R.H.S. Colour Chart of The Royal Horticultural Society of London (R.H.S.), 6$^{th}$ edition (2015).

Classification:
- *Family.*—Rosaceae.
- *Botanical.*—*Prunus laurocerasus.*
- *Common.*—Cherry laurel; English laurel.
- *Designation.*—'JOPRU3'.

Plant:
- *Type.*—Perennial, evergreen shrub.
- *Time to produce a finished plant.*—About 2 years from rooted cuttings to a sale-ready plant in a 2.5-liter container.
- *Appropriate container for producing a finished plant.*—2.5-liter pots and larger or field-grown.
- *Plant shape.*—Flattened globular.
- *Growth habit.*—Broad spreading-upright.
- *Average plant height.*—64.3 cm.
- *Average plant diameter.*—93.2 cm.
- *Growth rate.*—Moderately high.
- *Vigor.*—High

*High temperature tolerance*.—Unknown, but tolerant to temperatures up to 35° C.

*Low temperature tolerance*.—About −13° C., but at least hardy to USDA Zone 7.

*Disease/pest resistance and susceptibility*.—Similar to other *P. laurocerasus* varieties.

*Tolerance to wind*.—High.

Branches:

*Habit*.—Main stems grow from the base and near the base, with lateral branches.

*Basal branching*.—Present.

*Pinching*.—Not required but will improve branching.

*Number of branches per plant*.—17 primary or main branches and 13 secondary or lateral branches.

*Branch length* (*both main and lateral*).—Average is 24.7 cm.

*Branch diameter* (*both main and lateral*).—Average is 0.3 cm.

*Internode length* (*both main and lateral*).—Average is 2.6 cm.

*Appearance and shape*.—Moderately glossy; current year's lateral branches are angled and older branches are rounded.

*Aspect*.—Average angle of 35 degrees.

*Strength*.—Strong.

*Color*.—Immature: Upper part is RHS 146C (Yellow-Green) and slightly tinged with RHS 174A (Greyed-Orange) to RHS 174B (Greyed-Orange) and lower part is RHS 144B (Yellow-Green). Bark and older stems: RHS 143A (Green).

*Internode color*.—Slightly darker than RHS 143A (Green).

*Pubescence*.—Absent.

*Lenticels*.—General: Stems are sparsely covered with lenticels. Length: 0.5 mm. Diameter: 0.5 mm. Color: RHS 199C (Greyed-Brown) and RHS 199D (Greyed-Brown) on older stems and are RHS N199C (Greyed-Brown) on bark.

Leaves:

*Arrangement and type*.—Alternate, single.

*Number of leaves per branch*.—Average is 10.

*Shape*.—Narrow elliptic.

*Aspect*.—Flat.

*Apex*.—Long apiculate.

*Base*.—Attenuate.

*Margin*.—Slightly revolute, entire.

*Margin undulation*.—Slightly to moderately coarsely undulating; no lobing.

*Length*.—Average is 11.7 cm.

*Width*.—Average is 3.5 cm.

*Texture* (*both upper and lower surface*).—Smooth and glabrous; no pubescence; no rugosity.

*Appearance*.—Upper surface is glossy and lower surface is matte to very slightly glossy.

*Venation pattern*.—Pinnate.

*Venation color*.—Upper surface: RHS 144A (Yellow-Green) to RHS 144B (Yellow-Green). Lower surface: RHS 144B (Yellow-Green).

*Color*.—Immature: Upper surface: RHS 175A (Greyed-Orange). Lower surface: RHS 175C (Greyed-Orange) and fading to RHS 175D (Greyed-Orange) towards the main vein. Mature: Upper surface: Slightly darker than a blend of RHS N137A (Green) and RHS 147A (Yellow-Green). Lower surface: RHS 147B (Yellow-green).

*Petiole*.—Length: Average is 1.1 cm. Diameter: Average is 0.2 cm. Color: RHS 143B (Green) for the upper part margins are RHS 144B (Yellow-Green) and RHS 144A (Yellow-Green) for the lower part. Texture: Smooth and glabrous. Appearance: Upper part is slightly glossy and lower part is moderately glossy. Strength: High.

*Stipules*.—General: Present on both sides of the petiole base; stipules drop off when the leaves mature. Shape: Lanceolate. Length: 1.5 cm. Width: 0.2 cm. Apex: Narrow acute. Base: Cuneate. Margin: Sparsely, coarsely and shallowly serrate. Color: Upper part is RHS 150C (Yellow-Green) to RHS 145B (Yellow-Green) and lower part is RHS 145C (Yellow-Green).

*Glands*.—General: Present at the base of each leaf and 1 gland on each side of the main vein; the presence of these glands is typical for *P. laurocerasus* varieties. Diameter: 0.8 mm. Color: RHS 200C (Brown) and RHS 200B (Brown), but lighter.

*Fragrance*.—Typical of species.

Flowers/seed/fruit: Not observed to date.

COMPARISON WITH COMMERCIAL VARIETY

'JOPRU3' can be distinguished between the commercial variety 'Jong3' (U.S. Plant Pat. No. 29,891) in Table 1.

TABLE 1

Comparison with Commercial Variety

| Characteristic | 'JOPRU3' | 'Jong3' |
|---|---|---|
| Plant height | 64.3 cm | 72.0 cm |
| Plant diameter | 93.2 cm | 74.5 cm |

I claim:

1. A new and distinct variety of *Prunus laurocerasus* plant designated 'JOPRU3' as illustrated and described herein.

* * * * *